(12) United States Patent
Takemoto et al.

(10) Patent No.: US 10,384,379 B2
(45) Date of Patent: Aug. 20, 2019

(54) SYRINGE WITH NEEDLE (71) Applicant: TERUMO KABUSHIKI KAISHA, Tokyo (JP)

(72) Inventors: Masafumi Takemoto, Shizuoka (JP); Kozo Matsumoto, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 332 days.

(21) Appl. No.: 15/162,790

(22) Filed: May 24, 2016

(65) Prior Publication Data

US 2016/0271848 A1 Sep. 22, 2016

Related U.S. Application Data

(63) Continuation of application No. 13/814,788, filed as application No. PCT/JP2011/072040 on Sep. 27, 2011, now abandoned.

(30) Foreign Application Priority Data

Sep. 29, 2010 (JP) .................................. 2010-218300

(51) Int. Cl.
*B29C 45/14* (2006.01)
*A61M 5/34* (2006.01)
(Continued)

(52) U.S. Cl.
CPC ......... *B29C 45/14065* (2013.01); *A61M 5/34* (2013.01); *A61M 5/343* (2013.01);
(Continued)

(58) Field of Classification Search
CPC .... B29C 45/14065; B29C 2045/14139; A61M 5/34; A61M 2207/00
See application file for complete search history.

(56) References Cited

U.S. PATENT DOCUMENTS 2,708,438 A * 5/1955 Cohen .................. A61M 5/284
604/192
4,961,728 A 10/1990 Kosinski
(Continued)

FOREIGN PATENT DOCUMENTS

GB 2352403 1/2001
JP 63-117550 7/1988
(Continued)

OTHER PUBLICATIONS

International Search Report for PCT/JP2011/072040 with English-language Translation dated Dec. 27, 2011.
(Continued)

*Primary Examiner* — Laura A Bouchelle
(74) *Attorney, Agent, or Firm* — Greenblum & Bernstein, P.L.C.

(57) ABSTRACT

A method of assembling a syringe with needle is provided. The method may include preparing a mold for forming a tube hole of a main body of the syringe, a first part and a second part for forming a connection part of the syringe, and a third part for forming a close contact part of the syringe, supporting and securing a proximal portion of a needle tube by the mold, injecting the resin into the mold, and forming the syringe and the needle tube integrally by forming the syringe around the needle tube.

10 Claims, 5 Drawing Sheets

(51) Int. Cl.
  *B29L 31/00* (2006.01)
  *A61M 5/32* (2006.01)
  *B29K 101/12* (2006.01)
  *B29K 705/02* (2006.01)
  *B29K 705/08* (2006.01)
  *B29K 705/12* (2006.01)

(52) U.S. Cl.
  CPC ....... *A61M 5/3202* (2013.01); *A61M 2207/00* (2013.01); *B29K 2101/12* (2013.01); *B29K 2705/02* (2013.01); *B29K 2705/08* (2013.01); *B29K 2705/12* (2013.01); *B29L 2031/7544* (2013.01)

(56) References Cited

U.S. PATENT DOCUMENTS

| | | | |
|---|---|---|---|
| 5,483,027 | A | 1/1996 | Krause |
| 5,685,866 | A | 11/1997 | Lopez |
| 6,589,261 | B1 | 7/2003 | Abulhaj et al. |
| 2004/0243165 | A1 | 12/2004 | Koike et al. |
| 2005/0240207 | A1 | 10/2005 | Marshall |
| 2007/0185460 | A1 | 8/2007 | Vedrine et al. |
| 2009/0281562 | A1 | 11/2009 | Sarna et al. |
| 2010/0145284 | A1* | 6/2010 | Togashi ............ A61M 5/346 604/218 |
| 2010/0270702 | A1 | 10/2010 | Zelkovich et al. |
| 2012/0010573 | A1 | 1/2012 | Lundquist |
| 2012/0179113 | A1 | 7/2012 | Yokota et al. |

FOREIGN PATENT DOCUMENTS

| | | |
|---|---|---|
| JP | 2-215474 | 8/1990 |
| JP | 8-597 | 1/1996 |
| JP | 2006-116163 | 5/2006 |
| JP | 2007-503866 | 3/2007 |
| JP | 2008-229328 | 10/2008 |
| JP | 2008-307423 | 12/2008 |
| WO | 2004/000118 | 12/2003 |
| WO | 2005/025641 | 3/2005 |
| WO | 2007/111519 | 10/2007 |
| WO | 2008/139982 | 11/2008 |
| WO | 2009/091895 | 7/2009 |
| WO | 2011/040221 | 4/2011 |

OTHER PUBLICATIONS

European Search Report for EP 11829097.2 dated Mar. 11, 2014.
Office Action issued in Japan Counterpart Patent Appl. No. 2012-536467, dated Aug. 28, 2015, along with an English translation thereof.
Office Action issued in Japan Counterpart Patent Appl. No. 2018-006260, dated Oct. 23, 2018, along with an English translation thereof.
Office Action issued in Japan Counterpart Patent Appl. No. 2016-100221, dated Apr. 26, 2017, along with an English translation thereof.
First Office Action issued in China Counterpart Patent Appl. No. 201180040416.0, dated Jun. 20, 2014, along with an English translation thereof.
Second Office Action issued in China Counterpart Patent Appl. No. 201180040416.0, dated Jan. 16, 2015, along with an English translation thereof.
Third Office Action issued in China Counterpart Patent Appl. No. 20118004016.0, dated Jul. 8, 2015, along with an English translation thereof.

* cited by examiner

SYRINGE WITH NEEDLE

CROSS-REFERENCE TO RELATED APPLICATION

This is a continuation application of pending U.S. patent application Ser. No. 13/814,788, filed on Feb. 7, 2013, which is a U.S. National Stage Application of International Application No. PCT/JP2011/072040, filed Sep. 27, 2011, which claims priority to Japanese Application No. 2010-218300, filed Sep. 29, 2010. The disclosures of these documents, including the specifications, drawings and claims, are incorporated herein by reference in their entirety.

TECHNICAL FIELD

The present invention relates to a syringe with needle such that a syringe is formed on a needle tube by insert molding.

BACKGROUND ART

In general, a syringe with needle includes a needle tube which is provided at a distal portion thereof with a needle tip capable of puncturing a living body, and a needle hub which holds the needle tube in a state of protruding the needle tip of the needle tube. In addition, the syringe with needle is configured by connecting a syringe to the needle hub. It is an existing practice to secure the needle tube to the needle hub by use of an adhesive in the condition where the needle tube is inserted and passed in an insertion hole of the needle hub (see, for example, Patent Document 1).

In recent years, there has been proposed a syringe with needle wherein a needle hub is omitted and a needle tube is secured directly to a syringe which is to be filled with a drug. In this syringe with needle, also, the needle tube is secured to the syringe by use of an adhesive, like in the existing syringe with needle.

PRIOR ART DOCUMENT

Patent Document

Patent Document 1: Japanese Patent Laid-open No. 2006-116163

SUMMARY OF INVENTION

Technical Problem

However, the syringe with needle wherein the syringe and the needle tube are secured by the use of the adhesive has had problems that the adhesive is needed and that an adhering step is needed after formation of the syringe. Therefore, the number of component parts is increased due to the adhesive, and the number of steps for assembly is increased, thereby leading to a rise in cost.

Furthermore, the syringe may be filled with a drug. Therefore, there have been problems that the adhesive used for securing the needle tube and the syringe may come into contact (liquid-liquid contact) with the drug placed in the syringe, thereby imposing a bad influence on the drug. In view of this, in recent years, as a new securing method in which an adhesive is not used, a technology for integrally forming a needle tube and a syringe by insert molding has been demanded.

In consideration of the above-mentioned problems, it is an object of the present invention to provide a syringe with needle wherein a needle tube and a syringe can be integrally formed by insert molding, without using any adhesive.

Technical Solution

In order to solve the above-mentioned problems and attain the object of the present invention, there is provided according to the present invention a syringe with needle, including: a needle tube having a needle tip capable of puncturing a living body; and a syringe formed integrally with the needle tube by insert molding. The syringe includes a main body which is filled with a drug, and a securing section which is formed to be continuous with the main body. The securing section secures the needle tube in a state that the needle tip of the needle tube is protruded. In addition, the securing section of the syringe has a holding hole in which a chuck member for supporting and securing a circumferential surface of the needle tube during the insert molding is inserted and passed.

Advantageous Effects

According to the syringe with needle of the present invention, the securing section of the syringe is formed therein with a holding hole in which the chuck member for supporting and securing the circumferential surface of the needle tube is inserted and passed. This enables the needle tube to be held from the side of the circumferential surface thereof, instead of both axial-directional ends thereof. This ensures that the needle tube can be assuredly held by the chuck member during the molding, so that the needle tube and the syringe can be integrally secured without using any adhesive and at accurate relative positions. In addition, the needle tube and the syringe can be integrally formed by the insert molding. This makes it possible to omit the step for adhering the needle tube and the syringe to each other, and to realize a reduction in cost.

Furthermore, the chuck member makes contact with that part of the needle tube which is covered by the securing section of the syringe, and does not make contact with that part (puncturing part) of the needle tube which is made to puncture a living body. Therefore, such troubles as marring of the puncturing part of the needle tube or deposition of dirt on the puncturing part can be prevented from being caused by the chuck member.

MODE FOR CARRYING OUT THE INVENTION

Now, an embodiment (exemplary mode) of a syringe with needle according to the present invention will be described below, referring to FIGS. 1 to 8. Incidentally, members shown in common in the drawings are denoted by the same reference symbols. Besides, the present invention is not to be restricted to the following embodiment (mode).

Incidentally, description will be made in the following order.
1. Configuration Example of Syringe with Needle
2. Assembly of Syringe with Needle
   1. Configuration Example of Syringe with Needle First, a syringe with needle according to an embodiment of the present invention (hereinafter referred to as "this embodiment") will be described with referring to FIGS. 1 to 7.

Figure 1:
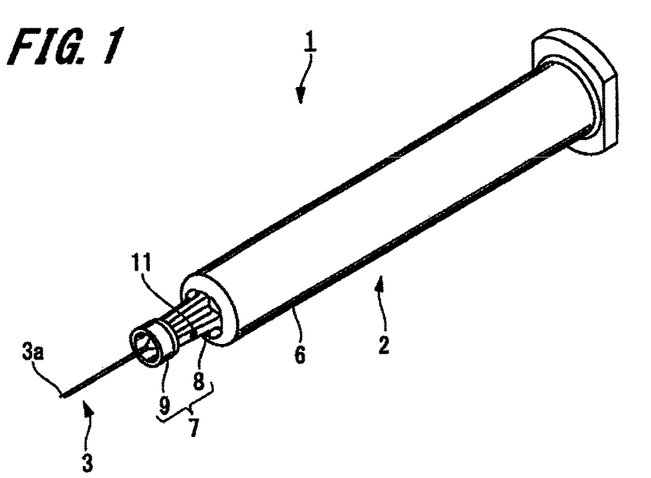
FIG. 1 is a perspective view showing an embodiment of a syringe with needle according to the present invention.
Figure 2:
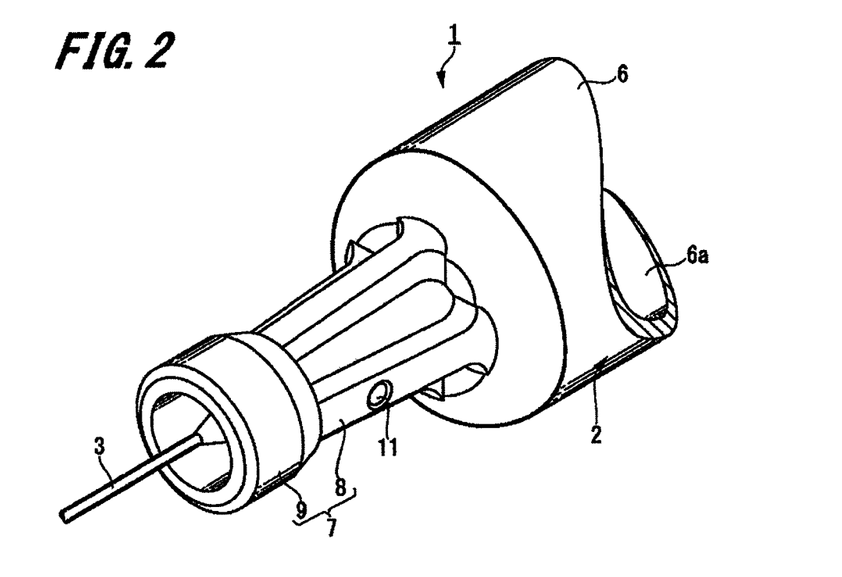
FIG. 2 is a perspective view showing a major part of the embodiment of the syringe with needle according to the present invention.
Figure 3:
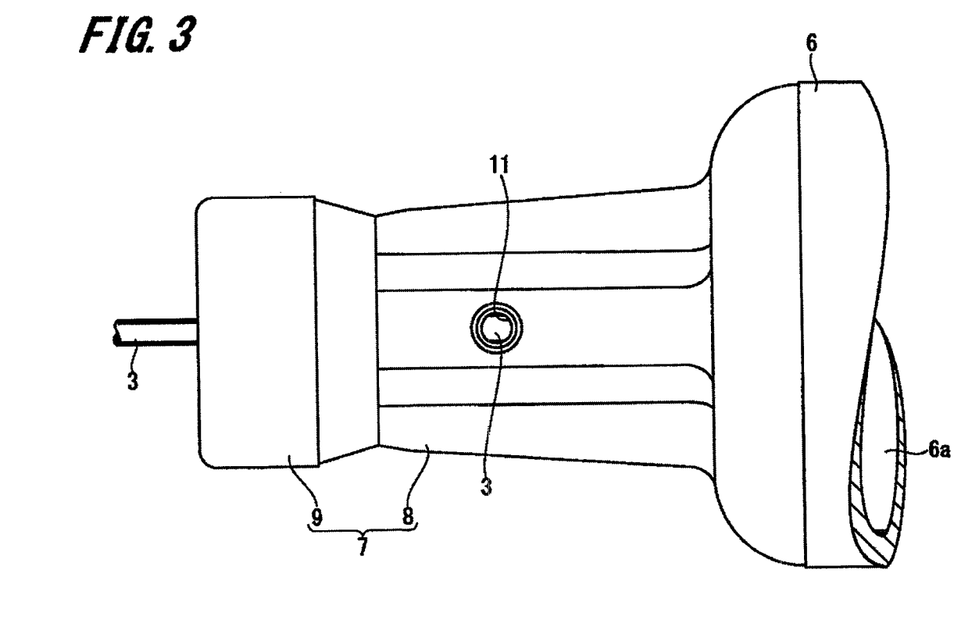
FIG. 3 is a side view showing a major part of the embodiment of the syringe with needle according to the present invention.
Figure 4:
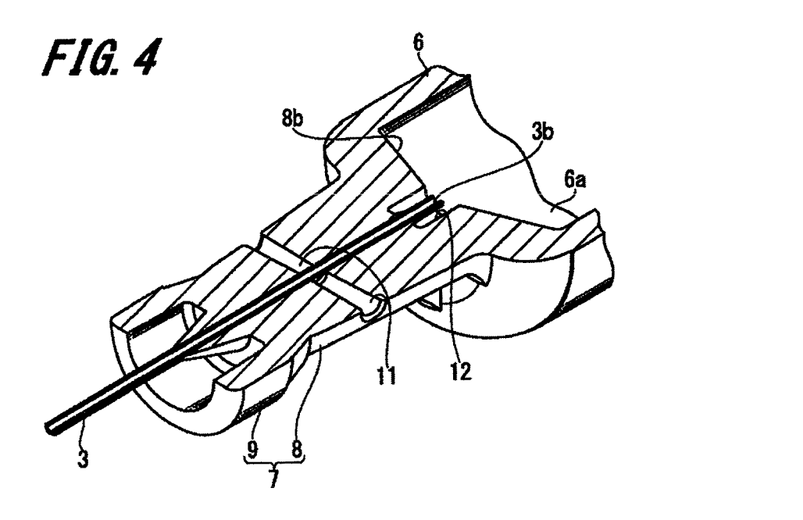
FIG. 4 is a perspective view showing, in section, a major part of the embodiment of the syringe with needle according to the present invention.
Figure 5:
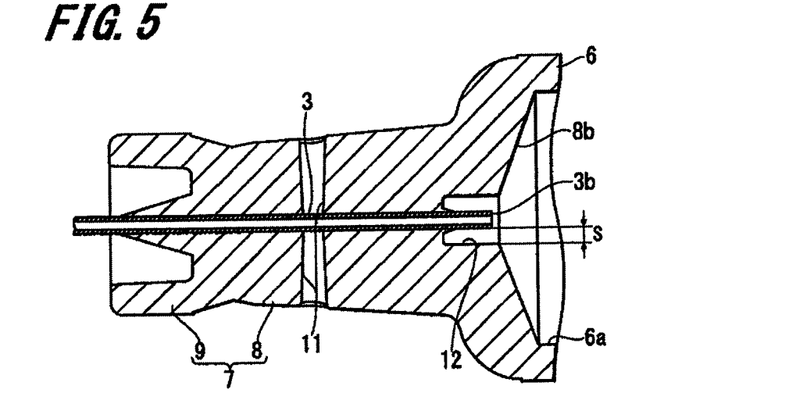
FIG. 5 is a sectional view showing a major part of the embodiment of the syringe with needle according to the present invention.

FIG. 1 is a perspective view showing a syringe with needle according to this embodiment, and FIG. 2 is a perspective view showing a major part of the syringe with needle in this embodiment. FIG. 3 is a side view showing the syringe with needle in this embodiment, and FIGS. 4 and 5 are sectional views showing the syringe with needle in this embodiment.

The syringe with needle, 1, is used to make a needle tip puncture a skin surface and to inject a drug into a living body. As shown in FIG. 1, this syringe with needle, 1, includes a syringe 2 which is filled with the drug, a needle tube 3 secured to the syringe 2, and a cap 4 (see FIGS. 6 and 7).

[Needle Tube]

First, the needle tube 3 will be described.

As the needle tube 3, a needle tube with a size (outside diameter: φ3.5 to 0.2 mm) of 10 to 33 gauge according to the ISO medical needle tube standard (ISO9626: 1991/Amd. 1:2001(E)) is used. Preferably, the size (outside diameter: φ1.7 to 0.2 mm) of 16 to 33 gauge is used. The needle tube 3 is formed, at one axial-directional end thereof, with a cutting edge for sharpening a needle tip 3a. The needle tip 3a on axial-directionally one side of the needle tube 3 is made to puncture a living body.

A material of the needle tube 3 may be, for example, stainless steel; however, this is not restrictive, and other metals such as aluminum, aluminum alloys, titanium, and titanium alloys can also be used as the material. In addition, the needle tube 3 is not limited to a straight needle, and may be a tapered needle which is tapered at least a part thereof. It suffices for the tapered needle to have a proximal portion greater in diameter than an end portion of the needle tip 3a and to have an intermediate portion of a tapered structure. Besides, a sectional shape of the needle tube 3 is not restricted to a circle but may be a polygon such as a triangle.

Furthermore, a coating agent such as a silicone resin or a fluoro-based resin is applied to the surface on the needle tip 3a side of the needle tube 3. This ensures that when the needle tube 3 punctures a living body, the friction between the skin and the needle tube can be reduced, and the pain attendant on the puncture can be alleviated.

The needle tube 3 is secured to the syringe 2, with the needle tip 3a in the state of protruding to the outside. The needle tip 3a on the axial-directionally one side of the needle tube 3 protrudes from the distal end (tip) of a securing section 7 of the syringe 2 which will be described later.

[Syringe]

Now, the syringe 2 will be described below.

The syringe 2 includes a main body 6 which is filled with the drug, and the securing section 7 provided continuously with the main body 6. The main body 6 is formed in a substantially cylindrical shape, the securing section 7 is formed on axial-directionally one side of the main body 6 in a continuous form, and the main body 6 is opened at its end on the axial-directionally other side. Besides, in the case of a prefilled syringe, a tube hole 6a (see FIG. 2) of the main body 6 is filled with the drug, and a gasket as a pusher (or plunger) is fitted into the main body 6 from the axial-directionally other side. Further, as shown in FIG. 4, the tube hole 6a of the main body 6 is in communication with a proximal portion 3b constituting an axial-directionally other end of the needle tube 3 secured to the securing section 7.

Incidentally, while an example wherein the shape of the main body 6 of the syringe 2 is the substantially hollow cylindrical shape has been described in this embodiment, the shape of the main body 6 may be a hollow tetragonal prism or hexagonal prism.

As shown in FIGS. 2 and 3, the securing section 7 protrudes from the axial-directionally one side of the main body 6 along the axial direction. The securing section 7 is formed integrally with the needle tube 3, in a state of protruding the needle tip 3a of the needle tube 3, by insert molding. With the needle tube 3 thus formed integrally with the securing section 7 of the syringe 2 by the insert molding, an adhering step using an adhesive can be omitted. In addition, since no adhesive is used, there is no risk that the adhesive might make contact with the drug placed in the syringe 2, thereby imposing a bad influence on the drug.

As shown in FIG. 4, the needle tube 3 is placed on the axis of the securing section 7 and along the axial direction. In addition, the securing section 7 has a connection part 8 provided continuously with one axial-directional end of the main body 6, and a close contact part 9 provided continuously with the connection part 8.

The connection part 8 is formed in the shape of a cross in a cross-section surface in the direction orthogonal to the axial direction of the main body 6. In addition, the diameter on the close contact part 9 side of the connection part 8 is smaller than the diameter of the close contact part 9. Therefore, the securing section 7 is in a constricted shape at its connecting portion between the connection part 8 and the close contact part 9. Incidentally, while the connection part 8 in this embodiment is formed to decrease in diametral size as one goes away from the main body 6, the connection part 8 may be continuous while being constant in diametral size.

Furthermore, the connection part 8 is formed therein with a holding hole 11 which communicates from a circumferential surface thereof to the needle tube 3 secured therein. As shown in FIGS. 4 and 5, the holding hole 11 is a through-hole orthogonal to the axis of the connection part 8. In the holding hole 11, a chuck member 26 for supporting and securing a circumferential surface of the needle tube 3 is inserted and passed (see FIG. 8). This ensures that, at the time of the insert molding, the needle tube 3 can be held in the direction orthogonal to the axial direction thereof. Therefore, the insert molding can be easily carried out, with the needle tube 3 in a stable state. As a result, the needle tube 3 can be prevented from being deformed or bent under the molding pressure.

Incidentally, while an example wherein one holding hole 11 is provided has been described in this embodiment, this structure is not restrictive, and not less than two holding holes may be provided. In the case where a plurality of holding holes are provided, the holding holes are preferably formed in the connection part 8 at roughly regular intervals along the axial direction of the needle tube 3.

In addition, as shown in FIG. 4, the connection part 8 is formed with a spacing hole 12 at its end portion on the main body 6 side, namely, at its axial-directionally other end portion 8*b* of the connection part 8. The spacing hole 12 is provided at the axis of the other end portion 8*b* of the connection part 8. In the spacing hole 12, is disposed a proximal portion 3*b* of the needle tube 3.

Further, the spacing hole 12 is spaced from the outer circumferential surface of the needle tube 3. Incidentally, a distance S from the inner surface of the spacing hole 12 to the outer circumferential surface of the needle tube 3 is set, for example, in the range of 0.3 to 1.0 mm. The structure in which the other end portion 8*b* is provided with the spacing hole 12 spaced from the outer circumferential surface of the needle tube 3 prevents a resin from entering through the proximal portion 3*b* of the needle tube 3 into a needle hole during the insert molding to plug up the needle hole. Incidentally, this spacing hole 12 is formed by a support part 21*a* which supports the proximal portion 3*b* of the needle tube 3 during the insert molding (see FIG. 8).

Incidentally, while an example in which the connection part 8 is formed in a cross shape for reducing the material thickness and securing strength has been described in this embodiment, this is not restrictive. For instance, the shape of the connection part 8 may be a roughly cylindrical shape, a tetragonal prism or a hexagonal prism.

The close contact part 9 is provided at one axial-directional end of the connection part 8, namely, on the distal side of the securing section 7. The close contact part 9 is formed in a roughly cylindrical shape. The needle tip 3*a* of the needle tube 3 protrudes from axial-directionally one side of the close contact part 9. The close contact part 9, on the axial-directionally one side, is opened in its portion other than an outer circumferential portion thereof and the periphery of the needle tube 3, for the purpose of reducing the material thickness thereof. It is to be noted, however, that the purpose can be fulfilled without providing the opening. In addition, the outer circumferential surface of the close contact part 9 makes close contact with an inner circumferential surface of the cap 4 described later.

Incidentally, while an example in which the close contact part 9 is formed in the roughly cylindrical shape has been described, the shape of the close contact part 9 may be a tetragonal prism or a hexagonal prism insofar as it corresponds to the shape of a tube hole 4*a* of the cap 4.

Examples of a material of the syringe 2 having the above-mentioned configuration include various resins such as polyvinyl chloride, polyethylene, polypropylene, cyclic polyolefins, polystyrene, poly(4-methylpentene-1), polycarbonates, acrylic resins, an acrylonitrile-butadiene-styrene copolymer, polyesters such as polyethylene terephthalate, etc., a butadiene-styrene copolymer, and polyamides (e.g., nylon 6, nylon 6•6, nylon 6•10, nylon 12). Among these, preferred are such resins as polypropylene, cyclic polyolefins, polyesters, and poly(4-methylpentene-1). Incidentally, it is preferable for the material of the syringe 2 to be substantially transparent, for securing inside visibility.

The drug with which the syringe 2 is filled may be any drug that is ordinarily used as an injection agent. Examples of the drug include protein drugs such as antibodies, etc., peptide drugs such as hormones, etc., nucleic acid drugs, cell drugs, blood derivatives, vaccines for prevention of various infectious diseases, carcinostatic agents, anesthetics, narcotics, antibiotics, steroid preparations, proteinase inhibitors, heparin, saccharide injections such as glucose, etc., electrolyte correction injections such as sodium chloride, potassium lactate, etc., vitamin preparations, lipid emulsions, contrast media, and stimulants.

[Cap]

Figure 6:
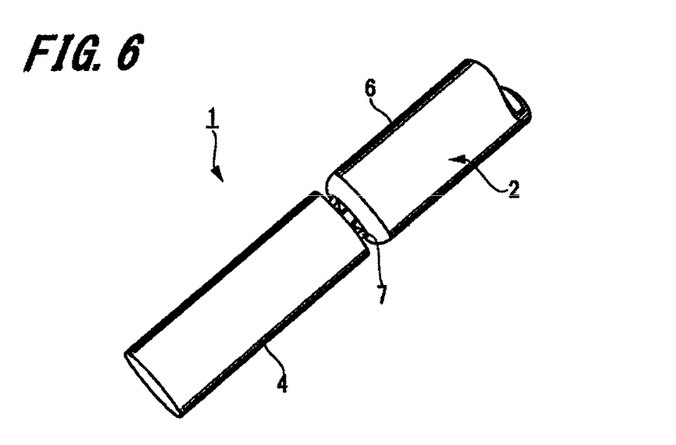
FIG. 6 is a perspective view showing a condition where a cap is mounted.
Figure 7:
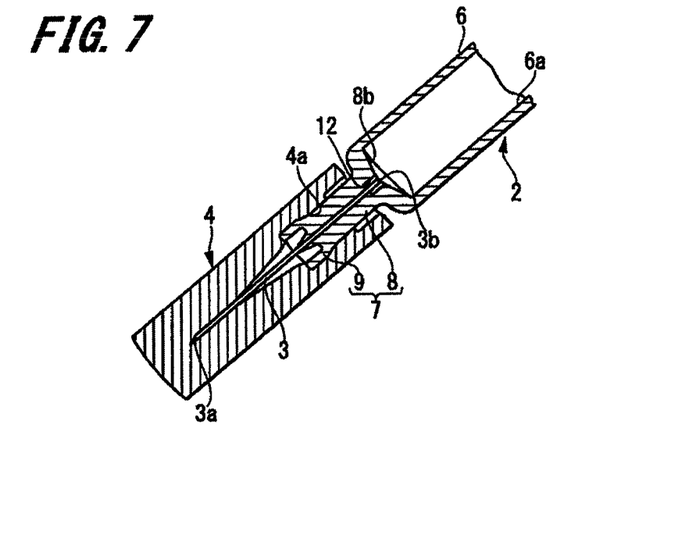
FIG. 7 is a sectional view of the syringe with needle and the cap shown in FIG. 6.

Now, the cap 4 will be described below. As shown in FIGS. 6 and 7, the cap 4 is formed in a roughly hollow cylindrical shape which is opened at one axial-directional end thereof and closed at the other axial-directional end thereof. The cap 4 is formed of an elastic material such as, for example, a rubber or an elastomer. As shown in FIG. 6, the cap 4 is mounted to axial-directionally one side of the syringe 2 in such a manner as to cover the needle tip 3*a* of the needle tube 3 and the securing section 7 of the syringe 2. In addition, as shown in FIG. 7, the needle tip 3*a* side of the needle tube 3 and the securing section 7 are inserted into the tube hole 4*a* of the cap 4.

Incidentally, the inside diameter of the tube hole 4*a* of the cap 4 is set to be approximately equal to or slightly smaller than the outside diameter of the close contact part 9 of the securing section 7. Therefore, when the cap 4 is mounted to the syringe 2, the outer circumferential surface of the close contact part 9 of the securing section 7 makes close contact with the inside circumferential surface of the cap 4. This ensures that the needle tip 3*a* side of the needle tube 3, which is on the distal side of the close contact part 9 of the securing section 7, is hermetically closed by the close contact part 9 and the inner circumferential surface of the cap 1. As a result deposition of bacteria on the needle tip 3*a* can be prevented.

In addition, the inner circumferential surface of the cap 4, by its elastic force, fastens a constricted portion at the connecting portion between the close contact part 9 and the connection part 8 of the securing section 7. As a result, the inner circumferential surface of the cap 4 and the constricted portion of the securing section 7 are engaged with each other, whereby the cap 4 can be prevented from slipping off from the syringe 2 during transportation.

2. Assembly of Syringe with Needle

Now, a method of assembling the syringe with needle, 1, configured as above will be described below referring to FIG. 8.

Figure 8:
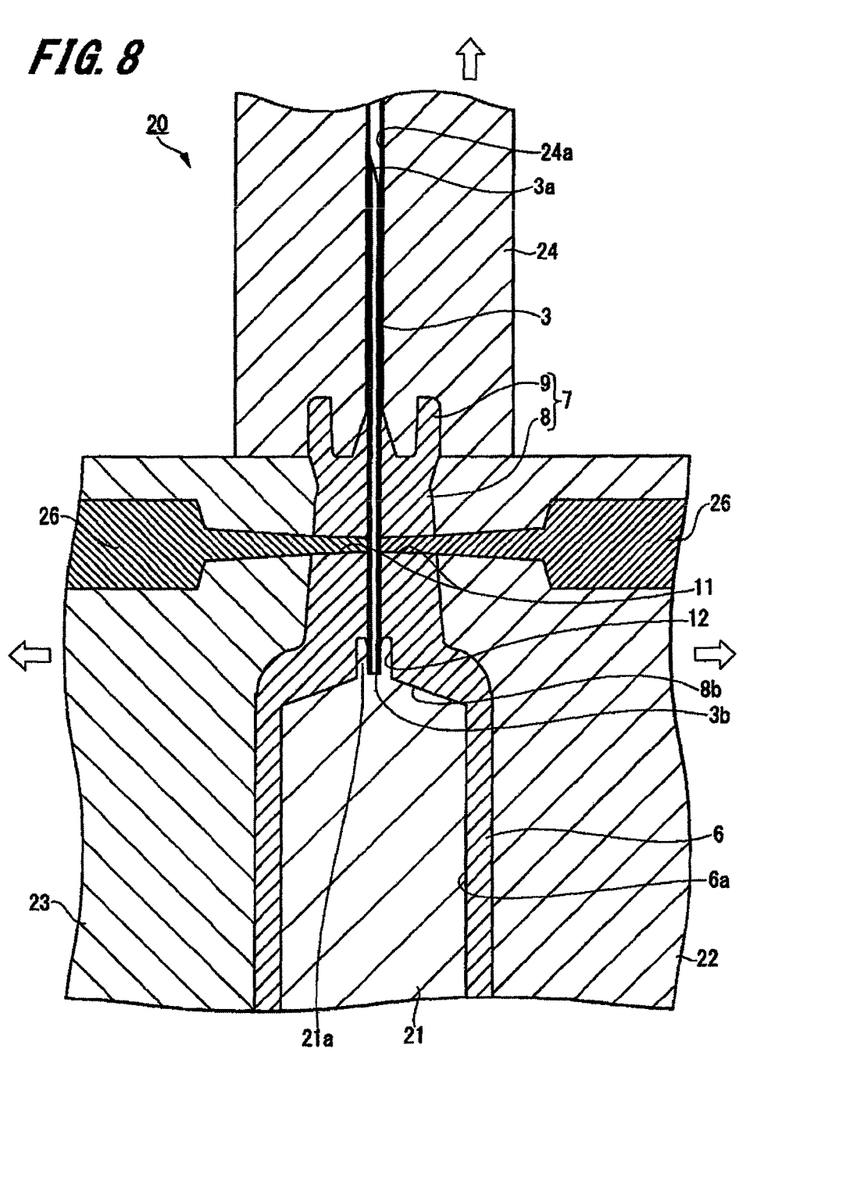
FIG. 8 is an illustration view showing a condition at the time of insert molding of the syringe with needle according to the present invention.

FIG. 8 is a sectional view showing a condition where the syringe with needle is formed by insert molding.

First, a mold 20 for molding the syringe with needle, 1, according to this embodiment will be described.

As shown in FIG. 8, the mold 20 includes a core 21 for forming the tube hole 6*a* of the syringe 2, a first part 22, a second part 23 opposed to the first part 22, and a third part 24 for forming the close contact part 9 of the syringe 2. The first part 22 and the second part 23 are each provided with the chuck member 26 for supporting and securing a side surface of the needle tube 3.

The chuck member 26 is provided at its tip with a V-shaped groove so that the needle tube 3 can be easily supported thereby. Incidentally, the tip of the chuck member 26 may be formed with a curved surface slightly larger than the diameter of the needle tube 3, instead of being formed with the V-shaped groove. Further, an elastic body may be provided at the tip of the chuck member 26 so that the needle tube 3 is prevented from being smashed or being marred on its side surface. Incidentally, the provision of the elastic body at the tip of the chuck member 26 makes it possible to flexibly cope with variability of the diametral size of the needle tube 3.

The core 21 is formed at its tip with a support part 21a for supporting and securing the proximal portion 3b of the needle tube 3. Besides, the third part 24 is formed therein with a guide hole 24a into which the needle tip 3a side of the needle tube 3 is inserted.

Incidentally, the joints between the first part 22 and the second part 23 and the third part 24 are located on the connection part 8 of the securing section 7 of the syringe 2.

The method of assembling the syringe with needle, 1, by use of the above-mentioned mold 20 is carried out as follows.

First, as shown in FIG. 8, the proximal portion 3b of the needle tube 3 is supported and secured by the support part 21a of the core 21. Similarly, the side surface of the needle tube 3 is supported and secured by the chuck members 26 of the first part 22 and the second part 23. Next, the needle tip 3a of the needle tube 3 is inserted into the guide hole 24a of the third part 24, and the needle tube 3 is set straight in relation to the mold 20. This makes it possible to prevent the needle tube 3 from being deformed during the molding, and to prevent the relative positions of the syringe 2 and the needle tube 3 from being erroneously changed.

Subsequently, a resin is poured into the mold 20, thereby performing the insert molding. As a result, the syringe 2 is formed around the needle tube 3. In this instance, the securing section 7 of the syringe 2 is formed therein with the holding hole 11, in which the chuck members 26 have been inserted and passed, and with the spacing hole 12. Then, the cap 4 is put on the needle tube 3 and the syringe 2. In this way, the assembly of the syringe with needle, 1, is completed.

Thus, the needle tube 3 and the syringe 2 can be integrally formed by the insert molding. This ensures that an adhering step using an adhesive can be omitted, and simplification of the assembling step can be achieved. Accordingly, a reduction in cost of assembly can be realized.

In addition, a part where the chuck members 26 support and secure the needle tube 3 becomes an intermediate part of the securing section 7 of the syringe 2 after the insert molding. Further, a part where a support part of the core 21 supports and secures the needle tube 3 is the proximal portion 3b on the side opposite to the needle tip 3a. This part is not that part (hereinafter referred to as "puncturing part") of the needle tube 3 is made to puncture a living body. Thus, the puncturing part of the needle tube 3 is not supported or secured during the insert molding; therefore, such troubles as adhesion of dirt onto the puncturing part or generation of mars on the side surface of the puncturing part can be prevented from occurring due to the chuck members 26 or the support part 21a of the core 21.

Furthermore, the needle tube 3 is supported and secured at three points by the chuck members 26 and the support part 21a of the core 21. This eliminates the need to support the needle tip 3a of the needle tube 3. Therefore, the needle tip 3a can be prevented from being damaged by the mold or the chuck members 26 or the like during the molding.

As above-mentioned, the joints between the first part 22 and the second part 23 and the third part 24 are located on the connection part 8 of the securing section 7 of the syringe 2. Therefore, a so-called parting line related to the mold is not formed on the close contact part 9 which is brought into close contact with the inner surface of the cap 4.

Thus, generation of burrs on the close contact part 9 can be prevented. This ensures that when the cap 4 is mounted in position, generation of a gap between the close contact part 9 and the inner surface of the cap 4 due to the presence of burrs is prevented. Consequently, air-tightness at the needle tip 3a of the needle tube 3 disposed on the distal side of the close contact part 9 can be maintained, and the needle tip 3a of the needle tube 3 can also be protected in a sterile state.

Incidentally, the present invention is not restricted to the embodiments described above and illustrated by the drawings, and various modifications are possible within the scope of the gist of the invention as defined by the claims.

EXPLANATION OF REFERENCE SYMBOLS

1 . . . Syringe with needle, 2 . . . Syringe, 3 . . . Needle tube, 3a . . . Needle tip, 3b . . . Proximal portion, 4 . . . Cap, 4a . . . Tube hole, 6 . . . Main body, 6a . . . Tube hole, 7 . . . Securing section, 8 . . . Connection part, 8b . . . Other end portion, 9 . . . Close contact part, 11 . . Holding hole, 12 . . . Spacing hole, 20 . . . Mold, 21 . . . Core, 21a . . . Support part, 26 . . . Chuck member.

What is claimed is:
1. A method of assembling a syringe with needle, the syringe with needle comprising: a needle tube having a needle tip configured to puncture a living body; an insert molded syringe provided integrally with the needle tube and formed of a resin, the syringe including a main body provided with a tube hole which is filled with a drug and a securing section which is formed to be continuous with a distal end of the main body, and the securing section securing the needle tube in a state that the needle tip of the needle tube is protruded in a distal direction of the securing section; and a cap configured to be mounted to a distal end of the syringe, the cap having a hollow cylindrical shape which is opened at one end thereof and closed at another end thereof, wherein the securing section of the syringe has a close contact part from which the needle tip of the needle tube protrudes in the distal direction of the securing section and a connection part which connects the close contact part and the main body with each other, the close contact part having a diameter that is larger than a diameter of a reduced diameter portion of the connection part, the reduced diameter portion being formed integral with the close contact part, wherein the close contact part protrudes from an end of the reduced diameter portion to provide a free end of the close contact part, the method comprising:
preparing a mold including a core for forming the tube hole of the main body, a first part and a second part for forming the connection part, and a third part for forming the close contact part, wherein the core is provided with a support part for supporting and securing a proximal portion of the needle tube at one end thereof and the first part and the second part are arranged opposite to each other,
preparing the mold such that an interface, at which the third part meets both the first and the second parts, coincides with a position at which the reduced diameter portion meets the close contact part,
supporting and securing the proximal portion of the needle tube by the support part of the core,
injecting the resin into the mold, and
forming the syringe and the needle tube integrally by forming the syringe around the needle tube so as to form parting lines, which are derived from the interface at which the third part meets both the first and the second parts, on the connection part of the securing section, putting the cap on the needle tube and the syringe so that an outer circumferential surface of the close contact part makes close contact with an inner circumferential surface of the cap.

2. The method according to claim 1,
wherein the third part has a guide hole into which the needle tip of the needle tube is inserted, and
wherein before the injecting the resin into the mold, the needle tip of the needle tube is inserted into the guide hole of the third part, and the needle tube is set straight in relation to the mold.

3. The method according to claim 1,
wherein in the forming the syringe and the needle tube integrally, a spacing hole having an inner surface spaced from an outer circumferential surface of the needle tube by the range of 0.3 to 1.0 mm is formed at the proximal portion of the connection part by the support part of the core.

4. The method according to claim 1, wherein the third part is provided with a protruded part that defines an inner circumferential surface shape of the close contact part.

5. A method of assembling a syringe with needle, the syringe with needle comprising: a needle tube having a needle tip configured to puncture a living body; an insert molded syringe provided integrally with the needle tube and formed of a resin, the syringe including a main body provided with a tube hole which is filled with a drug and a securing section which is formed to be continuous with a distal end of the main body, and the securing section securing the needle tube in a state that the needle tip of the needle tube is protruded in a distal direction of the securing section; and a cap configured to be mounted to a distal end of the syringe, the cap having a hollow cylindrical shape which is opened at one end thereof and closed at another end thereof, wherein the securing section of the syringe has a close contact part from which the needle tip of the needle tube protrudes in the distal direction of the securing section and a connection part which connects the close contact part and the main body with each other, the method comprising:
preparing a mold including a core for forming the tube hole of the main body, a first part and a second part for forming the connection part, and a third part for forming the close contact part, wherein the core is provided with a support part for supporting and securing a proximal portion of the needle tube at one end thereof and the first part and the second part are arranged opposite to each other, and wherein each of the first part and the second part is provided with a chuck member for supporting and securing a side surface of the needle tube,
supporting and securing the proximal portion of the needle tube by the support part of the core,
supporting and securing the side surface of the needle tube by the chuck members of the first part and the second part,
injecting the resin into the mold, and
forming the syringe and the needle tube integrally by forming the syringe around the needle tube so as to form parting lines, which are derived from joints between the first part, the second part and the third part, on the connection part of the securing section,
putting the cap on the needle tube and the syringe so that an outer circumferential surface of the close contact part makes close contact with an inner circumferential surface of the cap.

6. The method according to claim 5,
wherein a part where the chuck members support and secure the needle tube is an intermediate part of the securing section of the syringe, and a holding hole to insert the chuck members is formed in the connection part.

7. The method according to claim 5,
wherein a tip of each chuck member is formed with a V-shaped groove.

8. The method according to claim 5,
wherein a tip of each chuck member is formed with a curved surface slightly larger than a diameter of the needle tube.

9. The method according to claim 5,
wherein an elastic body is provided at a tip of each chuck member.

10. The method according to claim 5, wherein the third part has a guide hole into which the needle tip of the needle tube is inserted, and
wherein before the injecting the resin into the mold, the needle tip of the needle tube is inserted into the guide hole of the third part, and the needle tube is set straight in relation to the mold.

* * * * *